(12) United States Patent
Silagy et al.

(10) Patent No.: US 9,005,084 B2
(45) Date of Patent: Apr. 14, 2015

(54) APPARATUS AND SYSTEMS FOR FINGER EXERCISE

(71) Applicants: Robert Silagy, Merrick, NY (US); Dennis Waldman, Waban, MA (US)

(72) Inventors: Robert Silagy, Merrick, NY (US); Dennis Waldman, Waban, MA (US)

(73) Assignee: Cognatus Innovations LLC, Waban, MA (US)

( * ) Notice: Subject to any disclaimer, the term of this patent is extended or adjusted under 35 U.S.C. 154(b) by 93 days.

(21) Appl. No.: 13/750,334

(22) Filed: Jan. 25, 2013

(65) Prior Publication Data

US 2013/0196825 A1    Aug. 1, 2013

Related U.S. Application Data

(60) Provisional application No. 61/591,040, filed on Jan. 26, 2012, provisional application No. 61/591,043, filed on Jan. 26, 2012.

(51) Int. Cl.
*A63B 21/00* (2006.01)
*A63B 23/16* (2006.01)
*A63B 21/02* (2006.01)
(Continued)

(52) U.S. Cl.
CPC ............... *A63B 23/16* (2013.01); *A63B 21/023* (2013.01); *A63B 21/05* (2013.01); *A63B 24/0075* (2013.01); *G06F 1/1626* (2013.01); *G09B 13/00* (2013.01); *A63B 21/0428* (2013.01); *A63B 2024/0068* (2013.01); *A63B 2071/0655* (2013.01); *A63B 2071/0683* (2013.01); *A63B 2071/0694* (2013.01); *A63B 2220/10* (2013.01);
(Continued)

(58) Field of Classification Search
USPC ............................................... 482/47, 121, 49
See application file for complete search history.

(56) References Cited

U.S. PATENT DOCUMENTS 1,229,658 A  *  6/1917  Sandow .......................... 482/50
3,738,651 A       6/1973  Norman et al.
(Continued)

FOREIGN PATENT DOCUMENTS

WO    WO 2007/035364    3/2007

OTHER PUBLICATIONS

Prohands Hand Exerciser by Prohands (1 page), www.prohands.net/products, visited on Jan. 25, 2013.
Planet Waves Varigrip Hand Exerciser by Planet Waves (5 pages), http://www.amazon.com/Planet-Waves-Varigrip-Adjustable-Exerciser/dp/B001OCGGEM, visited on Jan. 25, 2013.
(Continued)

*Primary Examiner* — Jerome w Donnelly
(74) *Attorney, Agent, or Firm* — Carter, DeLuca, Farrell & Schmidt, LLP

(57) ABSTRACT

An improved finger exerciser to exercise each finger individually by depressing directly against the resistance of a spring. Embodiments are described wherein the device includes an electronic controller in operative communication with individual finger exercise elements to sense exercise parameters and provide tactile feedback to a user. In embodiments, the disclosed finger exerciser is configured to communicate sensed measurements to an integrated controller and/or a mobile device, such as a distance each finger is pressed, speed, response time, repetition count, and so forth. In embodiments, the exerciser is configured to provide tactile feedback, such as vibration, to a user via the finger pads. The finger exerciser may receive communications from an integrated controller and/or mobile device to activate a tactile stimulator. In some embodiments, the finger exerciser includes one or more spatial sensors to monitor movement of the device and communicate spatial information to an integrated controller and/or mobile device.

31 Claims, 12 Drawing Sheets

(51) Int. Cl.
  *A63B 21/05* (2006.01)
  *A63B 24/00* (2006.01)
  *G06F 1/16* (2006.01)
  *G09B 13/00* (2006.01)
  *A63B 21/04* (2006.01)
  *A63B 71/06* (2006.01)

(52) U.S. Cl.
  CPC ....... *A63B 2220/40* (2013.01); *A63B 2220/805* (2013.01); *A63B 2225/50* (2013.01)

(56) References Cited

U.S. PATENT DOCUMENTS

| | | |
|---|---|---|
| 5,147,256 A | 9/1992 | Silagy |
| D352,754 S | 11/1994 | Silagy |
| 5,431,611 A | 7/1995 | Silagy |
| 6,007,460 A | 12/1999 | Young |
| 7,381,156 B2 | 6/2008 | Silagy |
| 2007/0060448 A1 | 3/2007 | Silagy |
| 2009/0318269 A1* | 12/2009 | D'Addario et al. ............. 482/47 |

OTHER PUBLICATIONS

Portable Green Light Tension Guitar Extend-O-Grip Hand Exerciser by Flanger (3 pages), http://www.amazon.com/Portable-Tension-Guitar-Extend-O-Grip-Exerciser/dp/B0095OVC5Y/ref=sr_1_6?s=musical-instruments&ie=UTF8&qid=1358777378&sr=1-6&keywords=hand+exerciser, visited on Jan. 25, 2013.
Portable Black Medium Tension Guitar Extend-O-Grip Hand Exerciser by Flanger (4 pages), http://www.amazon.com/Portable-Medium-Tension-Extend-O-Grip-Exereiser/dp/B0095ON2RU/ref=sr_1_3?s=musical-instruments&ie=UTF8&qid=1358777378&sr=1-3&keywords=hand+exerciser, visited on Jan. 25, 2013.
ENO EHF-01 Instrument Plastic Finger Training Device—Green by ENO (3 pages), http://dx.com/p/eno-ehf-01-instrument-plastic-finger-training-device-green-157865, visited on Jan. 25, 2013.
Everlast Hand & Finger Strengthener by Everlast (4 pages), http://www.amazon.com/Everlast-EX3782YE-aka-EV3782YE-Strengthener/dp/B0013N4BVM/ref=sr_1_77?ie=UTF8&qid=1358777888&sr=8-77&keywords=finger+exerciser, visited on Jan. 25, 2013.
Ruff Rider Ruff Grip Callus Builder Caps (Standard) by Ruff Rider (5 pages), http://www.amazon.com/Ruff-Rider-Callus-Builder-Standard/dp/B0002H0N6/ref=sr_1_15?ie=UTF8&qid=1358777750&sr=8-15&keywords=finger+exerciser, visited on Jan. 25, 2013.

* cited by examiner

APPARATUS AND SYSTEMS FOR FINGER EXERCISE

CROSS-REFERENCE TO RELATED APPLICATIONS

This application claims priority from, and the benefit of, U.S. Provisional Application Ser. No. 61/591,040, filed Jan. 26, 2012, and U.S. Provisional Application Ser. No. 61/591,043, filed Jan. 26, 2012, the entirety of each of which is hereby incorporated by reference herein for all purposes.

BACKGROUND

Finger exercising devices have found widespread use in strength and endurance training applications, as well as in therapeutic applications to overcome physiological dysfunction and injury. Various type of finger and hand exercise devices have been developed, such as a large v-spring having handles on either leg which are held in the hand and repeatedly squeezed together. Another device features two parallel handles which are urged apart by an arrangement of spring or elastomeric bands which are grasped between the thumb and forefingers and squeezed together. Yet another style of hand exerciser features individual spring-activated plungers and an opposing spring activated palm rest. Still others utilize a wristband or glove arrangement having an array of elastomeric tethers running from the fingers to an anchor point. Various other shapes and styles of squeezable foam rubber devices have also been used.

Conventional hand exercise devices may have drawbacks, because they rely upon the user to faithfully perform the necessary exercises to achieve a desired outcome, such as improved strength, dexterity, or recovery from dysfunction or injury. Moreover, conventional hand exercise devices have limitations in that they are passive devices which cannot effectively enable a therapist or trainer to monitor a user's progress or compliance with a prescribed exercise regimen.

SUMMARY

The present disclosure is directed to an improved finger exerciser. In embodiments, the disclosed finger exerciser includes a housing having an upper portion and a lower portion, a plunger assembly, and a grip. The plunger assembly includes a tubular shaft having a pad base defined at an upper end thereof that is configured to operably engage a finger pad, and a finger pad operably engaged with the pad base. An opening is defined in the upper portion of the housing that is configured to enable the tubular shaft to traverse therethrough. The disclosed finger exerciser includes a coil spring in operative association with the shaft that is configured to urge the shaft in an upward direction. The grip is defined in the lower portion and includes a first concave portion forming a thumb saddle defined in the grip, a second concave portion forming a finger saddle defined in the grip, and a convex portion forming a palm pad defined on the grip.

In some embodiments, the disclosed finger exerciser includes a generally tubular shaft guide configured to slidably extend into an inner bore of the tubular shaft. In some embodiments, the tubular shaft guide extends from a guide frame. In some embodiments, the coil spring is concentrically disposed between the inner bore of the tubular shaft and an outer surface of the shaft guide. In some embodiments, the disclosed finger exerciser further includes a controller configured to communicate with at least one of a linear position encoder and a transducer. The controller may include a data communication interface. In some embodiments, the disclosed finger exerciser further includes a linear position encoder in operative association with the shaft and in operable communication with the controller. In some embodiments, the linear position encoder comprises a scale fixed on an outer surface of the shaft having encoded indicia disposed thereupon, a light source configured to illuminate the scale, and a light detector configured to detect reflected light from the scale. In some embodiments, the finger exerciser a piezoelectric transducer fixed to the pad base and in operable communication with the controller. In some embodiments of the disclosed finger exerciser, the controller includes a processor, and a memory in operable communication with the processor and comprising a set of programmed instructions executable on the processor to vibrate the piezoelectric transducer in accordance with a predetermined pattern.

In another aspect, a finger exercising system is disclosed. In embodiments, the disclosed finger exercising system includes a finger exerciser that includes a housing having an upper portion and a lower portion, a plunger assembly including a tubular shaft having a pad base defined at an upper end thereof, wherein the pad base is configured to operably engage a finger pad, and a finger pad operably engaged with the pad base. An opening is defined in the upper portion of the housing that is configured to enable the tubular shaft to traverse therethrough. The finger exerciser includes a coil spring in operative association with the shaft that is configured to urge the shaft in an upward direction. The finger exerciser includes a grip defined in the lower portion that includes a first concave portion forming a thumb saddle defined in the grip, a second concave portion forming a finger saddle defined in the grip, and a convex portion forming a palm pad defined on the grip. The disclosed finger exercising system includes a controller configured to communicate with at least one of a linear position encoder, a spatial sensor, and a transducer and having a data communication interface configured to communicate with a remote handheld device. The disclosed finger exercising system includes a software application executable on a remote handheld device and configured to communicate with the controller to perform an action selected from the group consisting of receiving a linear position, receiving a spatial parameter, storing a linear position, storing a spatial parameter, displaying a linear position, displaying a spatial parameter, and transmitting a transducer command. In some embodiments, the spatial sensor is selected from the group consisting of a silicon accelerometer, a silicon gyroscope, and a silicon compass. In some embodiments, the software application is configured to communicate a linear position and/or a spatial parameter to an evaluating entity. In some embodiments, in the linear position encoder is configured to encode a position of the shaft. In some embodiments, a piezoelectric transducer is fixed to the pad base and is in operable communication with the controller and/or the software application.

In another aspect, a method of operating a hand exerciser is disclosed. In embodiments, the disclosed method includes providing a hand exerciser having a finger-actuatable plunger having a finger-contacting portion and a biasing member that urges the plunger against finger pressure, performing a gesture comprising depressing the finger-actuatable plunger to initiate an exercise routine, and causing the finger contacting portion of the plunger to vibrate. In some embodiments, causing the finger contacting portion of the plunger to vibrate includes vibrating the finger contacting portion of the plunger in a predetermined pattern corresponding to the exercise routine. In some embodiments, the method includes selecting an exercise routine from a set of predetermined exercise routines in response to the performed gesture. In some embodiments, the method includes measuring a displacement of the shaft and/or a velocity of the shaft. In some embodiments, the method includes wirelessly communicating the measured displacement and/or velocity to a remote device.

BRIEF DESCRIPTION OF THE DRAWINGS

Example embodiments in accordance with the present disclosure are described herein with reference to the drawings wherein.

DETAILED DESCRIPTION

Figure 1:
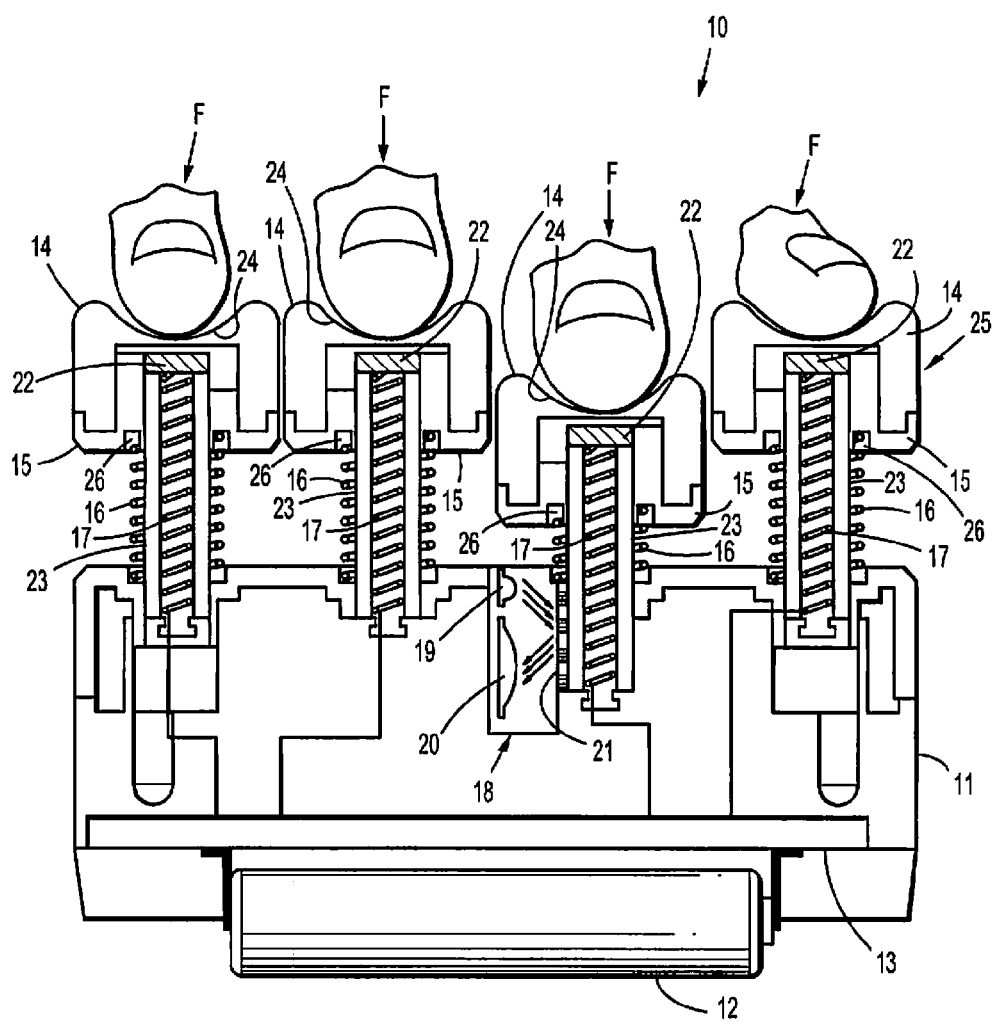
FIG. 1 is a cross-sectional view of an embodiment of an improved finger exerciser in accordance with the present disclosure.

Particular embodiments of the present disclosure are described hereinbelow with reference to the accompanying drawings; however, it is to be understood that the disclosed embodiments are merely examples of the disclosure, which may be embodied in various forms. Well-known and/or repetitive functions and constructions are not described in detail to avoid obscuring the present disclosure in unnecessary or redundant detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. In addition, as used herein in the description and in the claims, terms referencing orientation, e.g., "top", "bottom", "upper", "lower", "left", "right", "clockwise", "counterclockwise", and the like, are used with reference to the figures and features shown and described herein. It is to be understood that embodiments in accordance with the present disclosure may be practiced in any orientation without limitation. In this description, as well as in the drawings, like-referenced numbers represent elements which may perform the same, similar, or equivalent functions.

Figure 2:
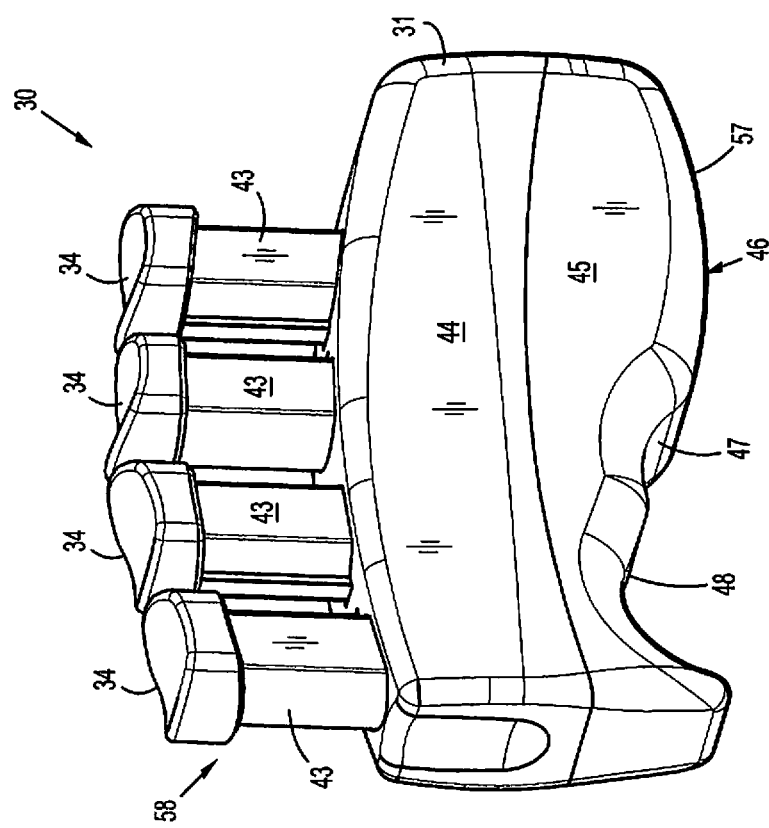
FIG. 2 is a perspective view of another embodiment of an improved finger exerciser in accordance with the present disclosure.
Figure 3:
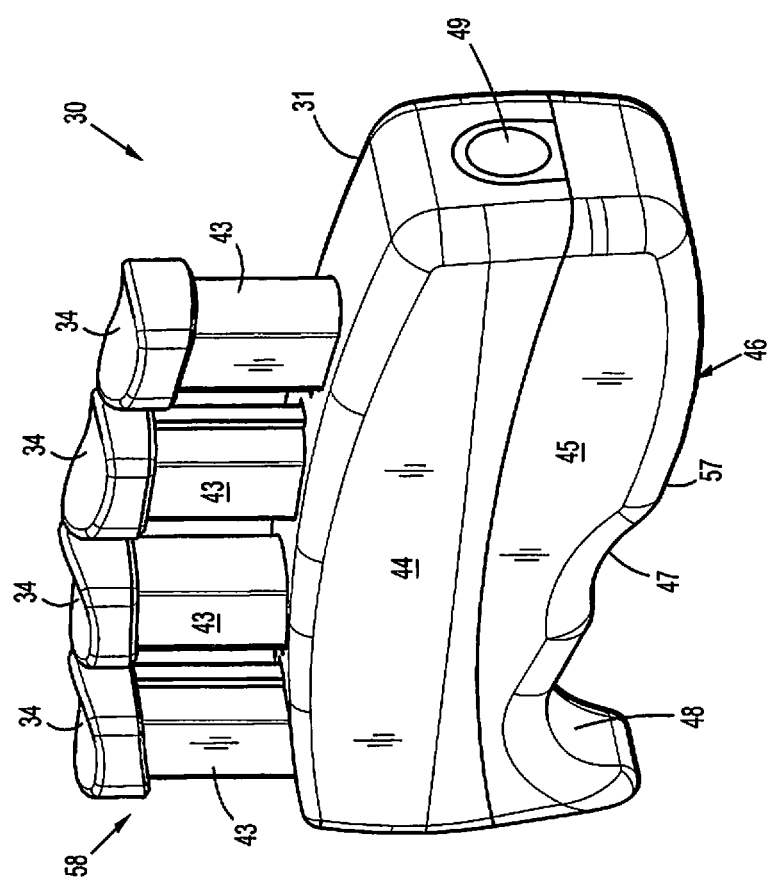
FIG. 3 is an alternative perspective view of the FIG. 2 embodiment of an improved finger exerciser in accordance with the present disclosure.

With reference to FIG. 1, an improved finger exerciser 10 is disclosed. The finger exerciser includes a housing 11 that supports one or more plunger assemblies 25 that are generally regularly spaced along a common centerline and which include a shaft 23 having a pad base 15 fixed to a top end of the shaft 23. A finger pad 14 having a recess 24 defined on an upper surface thereof is coupled to the pad base 15. Finger pad 14 and/or pad base 15 includes a transducer 22, such as without limitation, a piezoelectric transducer, which will be described in detail below. In some embodiments the finger pad 14 is selectively coupled to the pad base 15 to enable a user to easily swap finger pads 14 as desired. In embodiments, finger pad 14 is removably coupled to pad base 15 by a snap fitting. In embodiments, finger pad 14 and/or pad base 15 are indexed to ensure finger pad 14 is coupled to pad base 15 in a specific orientation, such as without limitation, where recess 24 is oriented generally transverse to the common center line of the shafts as shown in FIG. 1 and in the example embodiment depicted in FIG. 2. In embodiments, finger pad 14 and/or pad base 15 are configured to enable pad 14 to be affixed to pad base 15 in other orientations, such as without limitation where recess 24 is oriented generally longitudinally to the common center line of the shafts and/or where recess 24 is oriented at an arbitrary angle to the common center line of the shafts.

A compression spring 16 is disposed about a length of the shaft 23 and is configured to urge the shaft 23 in an upward direction. A top portion of spring 16 rests in a saddle 26 defined in a lower portion of pad base 15; a lower portion of spring 16 rests in a portion of housing 11. In use, a user's finger F bears down on a finger pad 14, overcoming the upward bias of spring 16 to depress plunger assembly 25 and thereby exercise finger F. As will be appreciated, the finger exerciser may be grasped by a user using one or more fingers of the hand to train the fingers individually or in any combination.

Improved finger exerciser 10 includes a controller 13 that is operably coupled to a linear optical encoder assembly 18, a power source 12, and to one or more transducers 22. Optical encoder assembly 18 is operably associated with a corresponding shaft 23 and is configured to communicate shaft position data to controller 13. Optical encoder 18 includes a light source 19 that is configured to illuminate a scale 21 affixed to shaft 23, and a light detector 20 configured to detect reflected light from scale 21 to enable controller 13 to ascertain the distance and/or speed at which each shaft is depressed. Scale 21 includes indicia disposed thereon, e.g., by printing, engraving, and the like, in regularly spaced intervals and/or in an encoded pattern, such as a quadrature or other pattern, to facilitate the detection of shaft 23 motion by light detector 20. In some embodiments, other linear motion detection and encoding assemblies and technologies may be advantageously employed, including without limitation, magnetic encoding, hall effect sensing, a transmissive optical detector wherein a shutter arrangement is used to modulate light emitted from light source 19 and received by light detector 20, a variable differential transformer, a potentiometer-based encoder, laser interferometer encoders, and so forth. In embodiments, light source 19 may include, without limitation, a light-emitting diode, laser diode, incandescent bulb, or other suitable light source. In embodiments, light detector 20 may include a photodiode, phototransistor, and/or any suitable light detection circuit element having the necessary bandwidth and/or response time to effectively detect the motion of shaft 23 when actuated by a user's finger. In some embodiments, light source 19 and light detector 20 may be included in a common housing.

Controller 13 is in operably coupled to transducer 22 by a conductor 17 disposed within a bore of shaft 23. In order to accommodate the up and down motion of shaft 23, conductor 17 may be formed from flexible conductive material, such as stranded wire, having a coiled construction. Conductor 17 may include one or more individual conducting elements separated by an insulator, e.g., a mini "coil cord", to effectively couple transducer 22 to controller 13. Transducer 22 is configured to impart mechanical vibrations into finger pad 14, thereby providing tactile communication to a user.

Figure 1A:
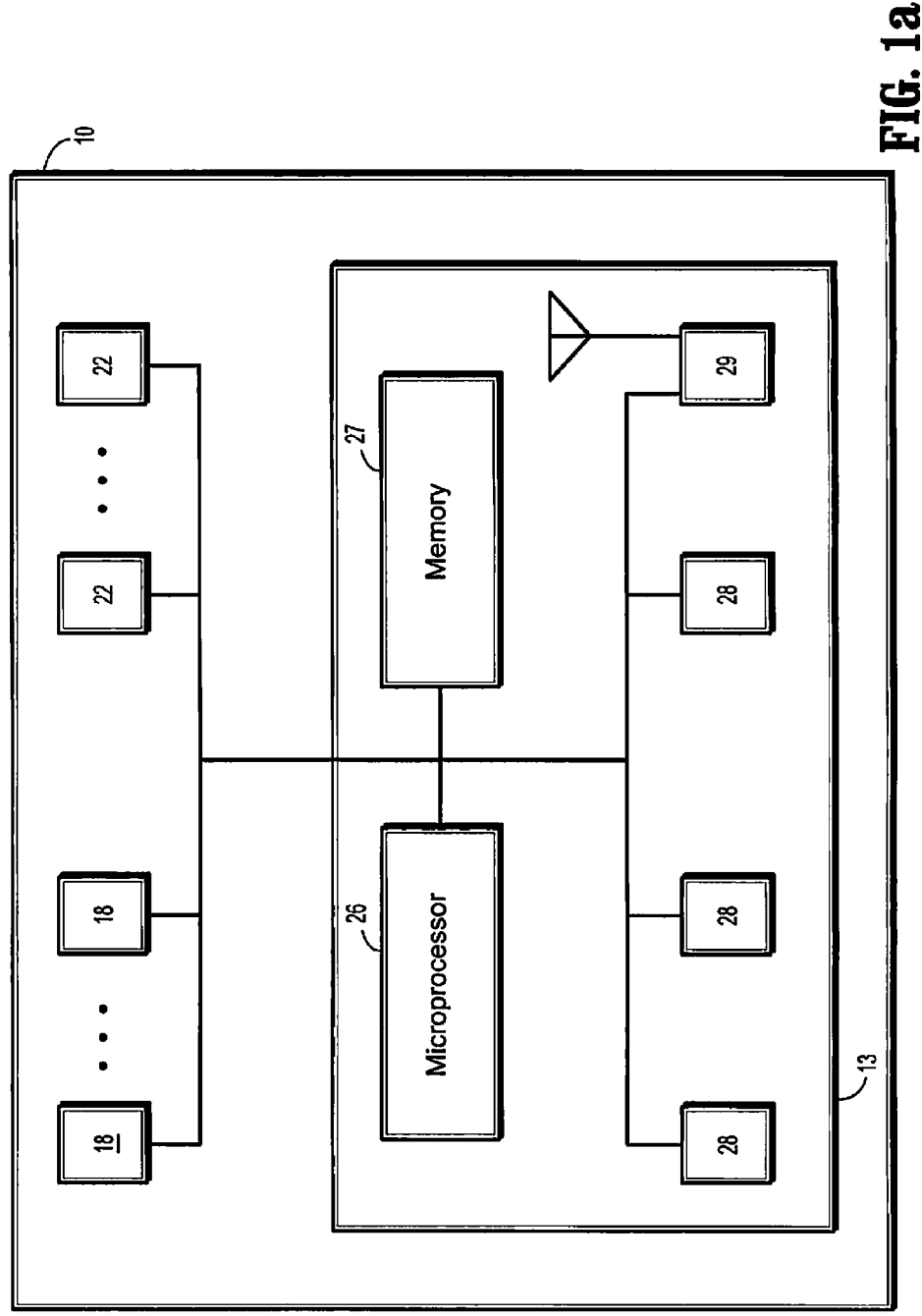
FIG. 1a is a block diagram of an embodiment of an improved finger exerciser in accordance with the present disclosure.

During use, the user may initiate an exercise routine by activating the controller by depressing one or more finger pads 14, and grasping finger exerciser 10 in the hand while placing the fingertip on the respective finger pads 14. Various exercise routines may be selected using a pushbutton, and/or using predetermined patterns of finger pad depression to communicate the user's selection to the controller 13. Additionally or alternatively, various levels of vibratory finger stimulation, various exercise speeds, and the like, may be selected in a similar manner. Controller 13 includes a microprocessor 26 (FIG. 1a) configured to execute a set of programmed instructions which is stored in memory 27, such as non-transitory memory, included in controller 13. Controller 13 may include a timeout function whereby the microprocessor enters a low-power standby state after a predetermined period of time has elapsed from an event such as a last finger pad depression or the completion of an exercise routine. In some embodiments, controller 13 may include a power up function that is activated by a user depressing one or more plunger assemblies 25.

Once an exercise routine has been activated, controller 13 communicates with a transducer 22, which, in turn, vibrates one or more finger pads 14 individually or in combination to indicate to the user via tactile stimulus which pad should be depressed. Additionally or alternatively, as the user depresses finger pads 14, and correspondingly, shaft 23, optical encoder 18 communicates positional information of the associated plunger assembly 25 to controller 13. In this manner, controller 13 may evaluate whether the user is dutifully and correctly performing the exercise routine. For example, and without limitation, controller 13 can determine if one finger is depressing the plunger associated therewith more slowly than the other fingers, conclude that the slow finger needs additional exercise, and modify the exercise routine by scheduling additional or more frequent tactile stimulus to the deficient finger during the exercise routine. In another embodiment, an exercise routine may be tailored to enhance dexterity for playing a particular musical instrument, for example, stringed instruments (guitar, bass, violin), brass instruments (trumpet, saxophone), keyboard instruments, and so forth. In some embodiments, a user may input a customized exercise routine into controller 13 by causing the controller to enter a programming mode, "playing" the desired routine, causing the controller to store the custom routine, and causing the controller to initiate the custom routine.

Tactile feedback may additionally or alternatively be employed to confirm that full depression of the plunger assembly 25 has been achieved, and/or may be used to provide massage therapy to the fingertip before, during, and following an exercise routine. In some embodiments, intensity of the tactile vibration may be modulated in response to speed and/or position of the plunger assembly 25.

In embodiments, controller 13 includes a data communication interface 29, such as a Bluetooth® interface, operably associated with the processor to facilitate communication with another device, such as a mobile device, smart phone, tablet computer, and so forth. Data communication interface 29 may communicate using wired, wireless, and/or optical techniques. In embodiments, controller 13 includes one or more spatial/positional sensors 28 operably associated with the processor, such as, without limitation, a silicon accelerometer, a silicon gyroscope, and/or a silicon compass.

Figure 10B:
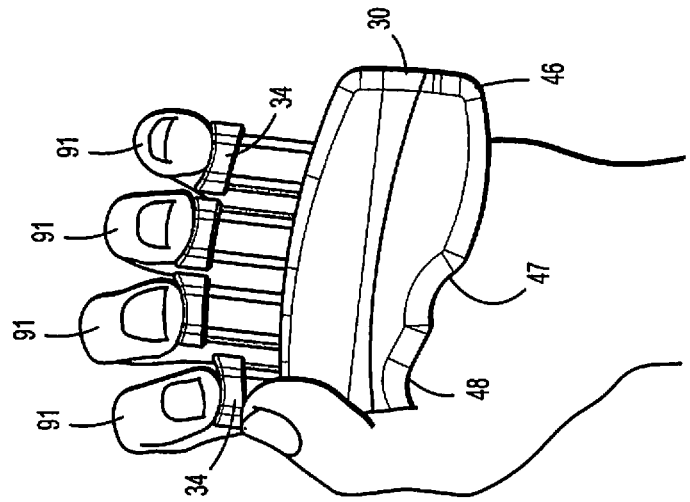
FIG. 10b is another view of an embodiment of an improved finger exerciser in use in accordance with the present disclosure.
Figure 10A:
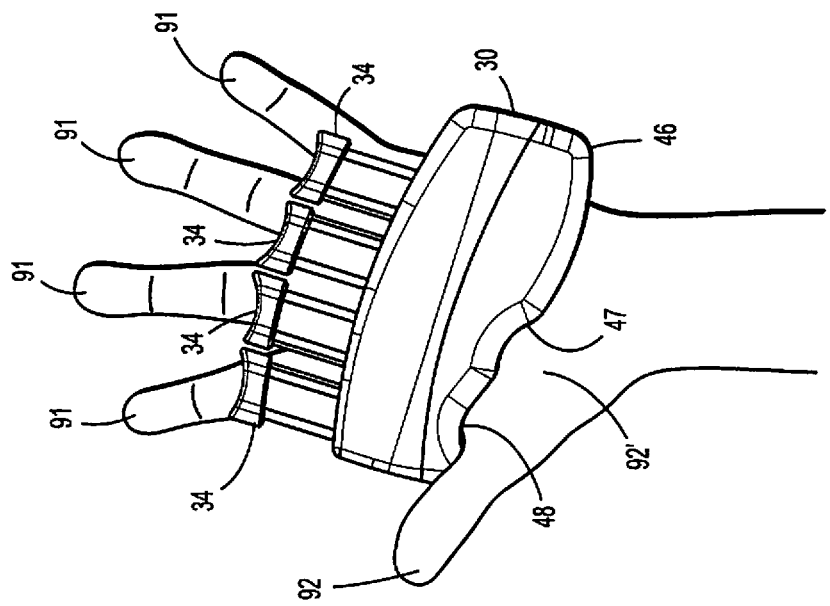
FIG. 10a is a view of an embodiment of an improved finger exerciser in use in accordance with the present disclosure.

Turning now to FIGS. 2-6, another embodiment of an improved finger exerciser 30 is illustrated. Finger exerciser 30 includes a housing 31 having an upper housing 44 and a lower housing 45. Lower housing includes a grip 46 having several features configured to improve the effectiveness of finger exercises performed with finger exerciser 30. Grip 46 includes a first concave portion forming a thumb saddle 47 defined therein that is configured to cooperate ergonomically with web 92' of a user's thumb 92 during use (see FIGS. 10a and 10b) and/or a user's forefinger (FIG. 10e). Grip 46 includes a second concave portion forming a finger saddle 48 defined therein that is configured to cooperate ergonomically with an upper portion of a user's thumb 92 during use (see FIGS. 10a and 10b) and/or a user's forefinger (FIG. 10e). Grip 46 includes a convex portion forming a palm pad 57 defined thereupon that is configured to cooperate ergonomically with a user's palm during use (FIGS. 10a, 10b). It is to be understood that the uses of thumb saddle 47, finger saddle 48, and palm pad 57 are not limited to the hand and finger placements described above, and may be used with any hand placements, finger placements, gripping styles, etc., as may be desired.

Finger exerciser 30 includes a guide frame 51 having one or more generally tubular shaft guides 50 extending therefrom, and one or more corresponding shafts 43 having a bore dimensioned to slidably receive shaft guide 50. A coil spring 36 positioned between shaft guide 50 and shaft 43 urges shaft 43 upwardly to provide the resistance required to perform finger exercises. In some embodiments, coil spring 36 is concentrically disposed between an outer diameter of shaft guide 50 and an inner diameter (e.g., bore diameter) of shaft 43. The rigidity and smoothness of motion of shaft 43 benefits from the internal support afforded by shaft guide 50, which, in turn, enables exercises to be performed with greater precision and comfort than with prior-art exercisers. An upper portion of shaft 43 includes a pad base 35 that is configured to operably couple to a finger pad 34. In embodiments, finger pad 34 is removable and/or interchangeable and may be indexed to ensure consistent positioning on pad base 35, as described above. Pad 34, pad base 35, and shaft 43 comprise plunger assembly 58. Advantageously, finger pad 34 may be removed to enable a user to change spring 36 to enable different levels of resistance. Spring 36 may be provided in various strengths, and may include a progressive winding that increases resistance as plunger assembly 58 is depressed. Additionally or alternatively, spring 36 may be changed by removing lower housing 45 from upper housing 44, removing guide frame 51 and/or controller 33, and swapping spring 36 from the bottom.

Upper housing 44 includes one or more openings 55 defined therein that are configured to enable plunger assembly 58 to move up and down therethrough. Opening 55 may include a notch 59 that is configured to engage a corresponding rib 60 provided on shaft 43. Advantageously, the described finger exerciser 30 design lends itself to a "bottom-up" assembly. A bottom-up assembly enables the device to be assembled rapidly, using no special tooling or jigs and requiring fewer parts, and with a decreased cost of production when contrasted to prior art devices having designs which dictate cumbersome and more costly "top-down" assembly requiring, for example, custom tooling to maintain parts in alignment during assembly.

Finger exerciser 30 includes a controller 33 that is operably coupled to a linear optical encoder assembly 38, a power source 32 operably coupled to controller 33 by one or more clips 54, and to one or more transducers 42 by a conductor 37. In order to accommodate the up and down motion of shaft 43, conductor 37 may be formed from flexible conductive material, such as stranded wire, having a coiled construction. Conductor 37 may include one or more individual conducting elements separated by an insulator, e.g., a mini "coil cord", to effectively couple transducer 42 to controller 33. Transducer 42 is configured to impart mechanical vibrations into finger pad 34, thereby providing tactile communication to a user.

Figure 4:
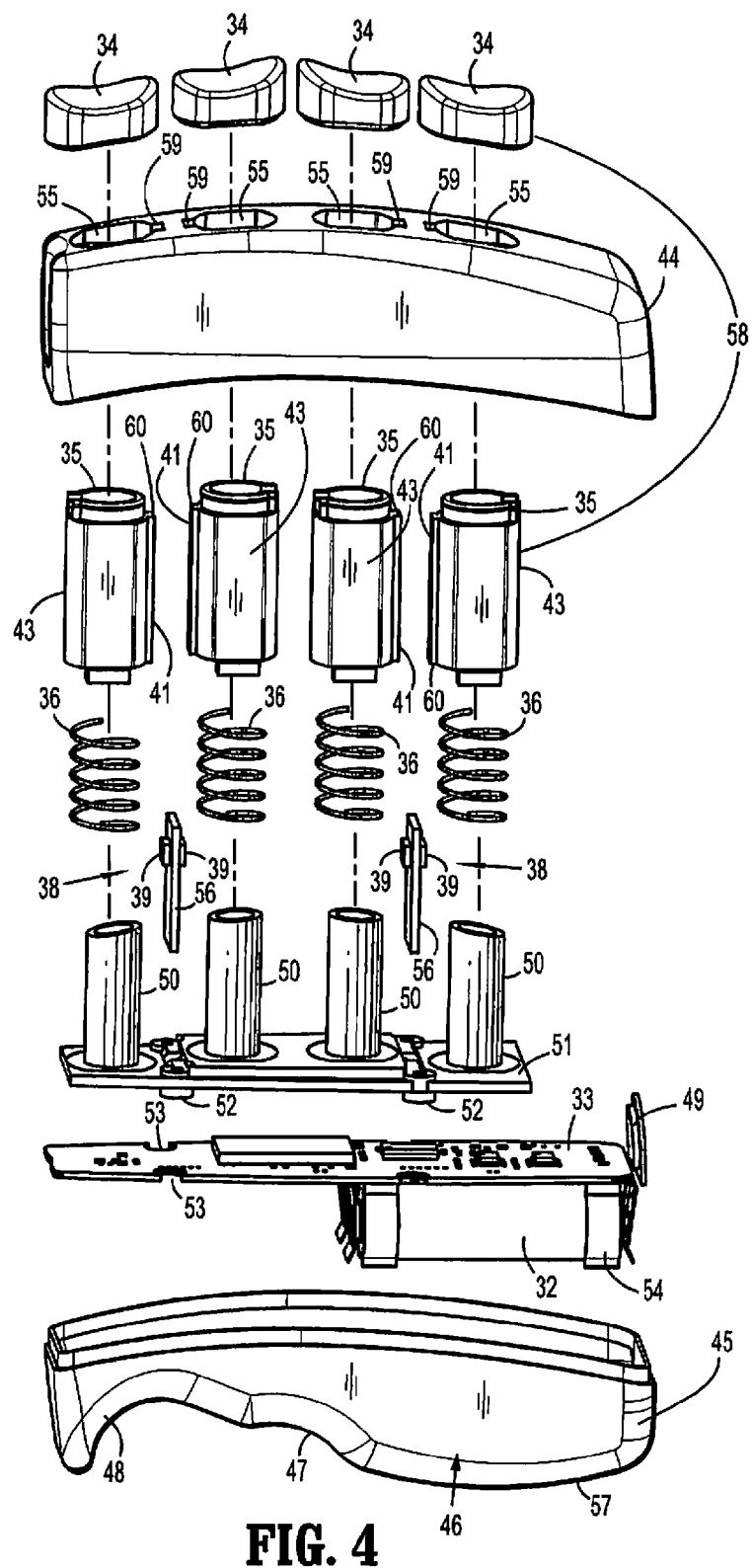
FIG. 4 is a side, exploded view of the FIG. 2 embodiment of an improved finger exerciser in accordance with the present disclosure.
Figure 5:
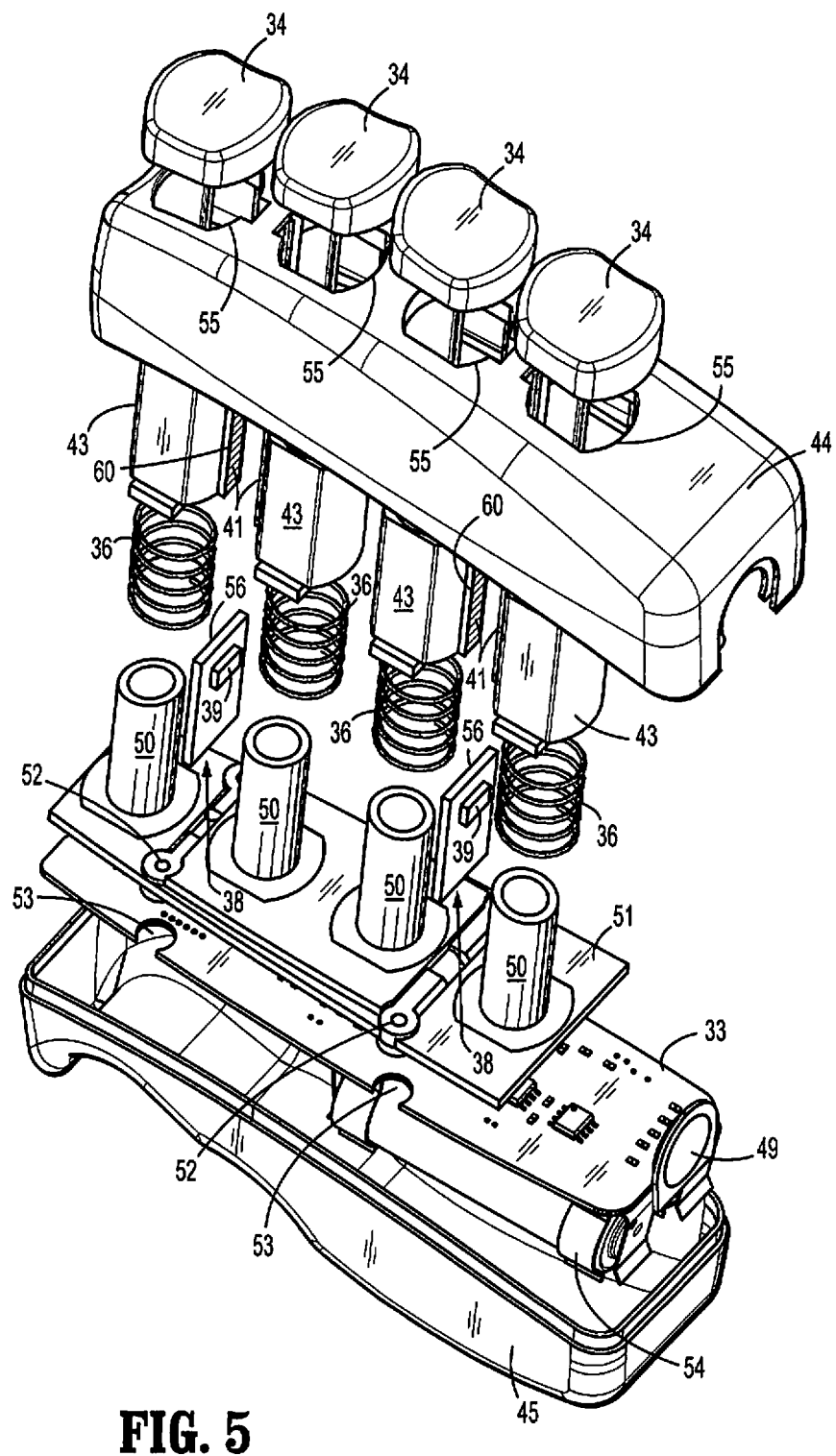
FIG. 5 is a perspective, exploded view of the FIG. 2 embodiment of an improved finger exerciser in accordance with the present disclosure.
Figure 6:
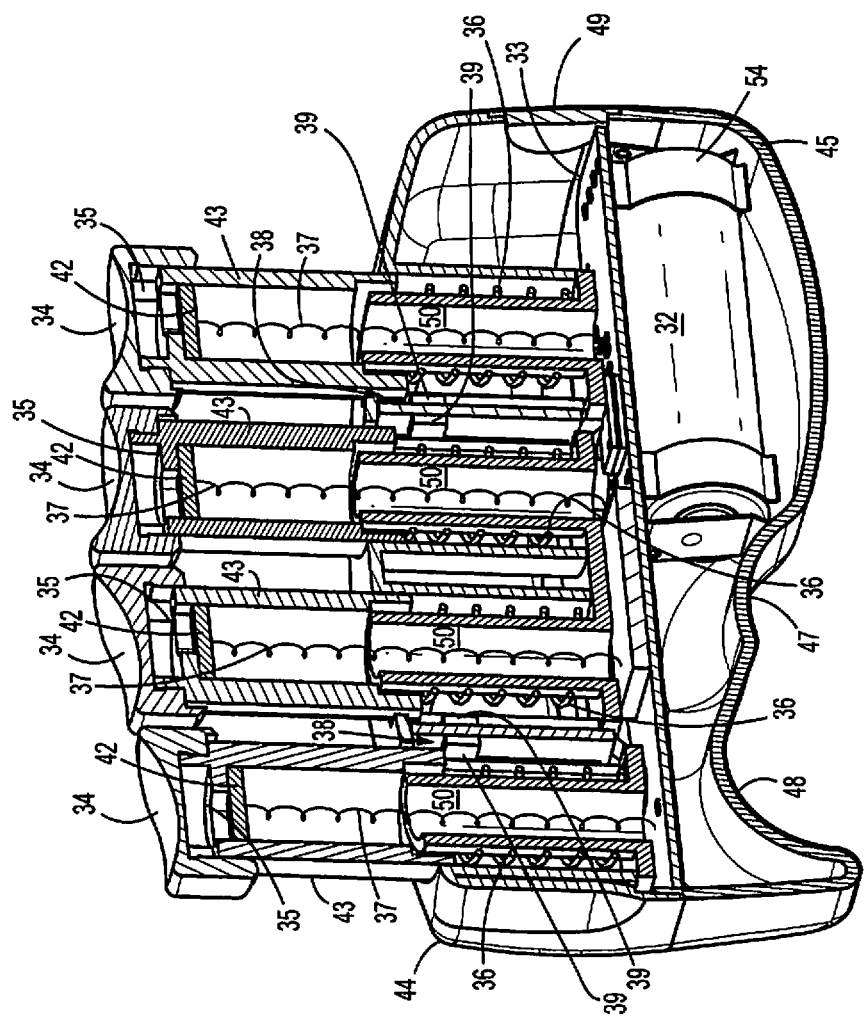
FIG. 6 is a side, cross-sectional view of the FIG. 2 embodiment of an improved finger exerciser in accordance with the present disclosure.

Optical encoder assembly 38 is operably associated with a corresponding shaft 43 and is configured to communicate shaft position data to controller 43. Optical encoder 38 includes a sensor mount 56 on which is mounted a positional sensor 39 that is configured to sense the linear motion of scale 41 that is affixed to shaft 43 to enable controller 33 to ascertain the distance and/or speed at which each shaft 43 is depressed. In embodiments sensor mount 56 may include a printed circuit board (PCB). In embodiments, positional sensor 39 may include a light transceiver comprising, e.g., a light source and a light detector. Scale 41 includes indicia disposed thereon, e.g., by printing, engraving, and the like, in regularly spaced intervals and/or in an encoded pattern, such as a quadrature or other pattern, to facilitate the detection of the movement of shaft 43 motion by positional sensor 39. Scale 41 may be annexed to rib 60, as shown in FIGS. 5 and 6. Optical encoder assembly 38 includes a tandem arrangement whereby sensor mount 56 includes a first positional sensor 39 mounted of first side of sensor mount 56 and a second positional sensor 39 mounted of second side of sensor mount 56, and where encoder assembly 38 is disposed between a pair of adjacent shafts 43. In this arrangement, the scales 41 of each shaft pair are oriented to face the corresponding positional sensor 39, as best seen in FIGS. 4, 5, and 6. Controller 33 may include a wireless communications interface and positional sensors as described above.

Optical encoder assembly 38 is fixed at a bottom edge thereof to guide frame 51. Guide frame 51 includes one or more tabs 52 that are configured to engage one or more corresponding slots 53 defined in controller 33. Controller 33 is operably coupled to a switch 49 that is configured to accept user inputs to controller 33, including but not limited to, power on/off, an exercise selection, an exercise parameter, a user identification, and so forth. In embodiments, switch 49 includes a snap dome contact.

Figure 7A:
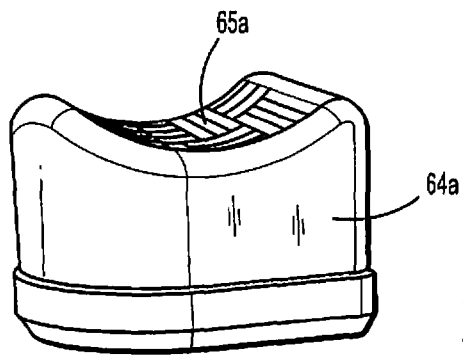
FIG. 7a is a view of an embodiment of a finger pad of an improved finger exerciser in accordance with the present disclosure.
Figure 7B:
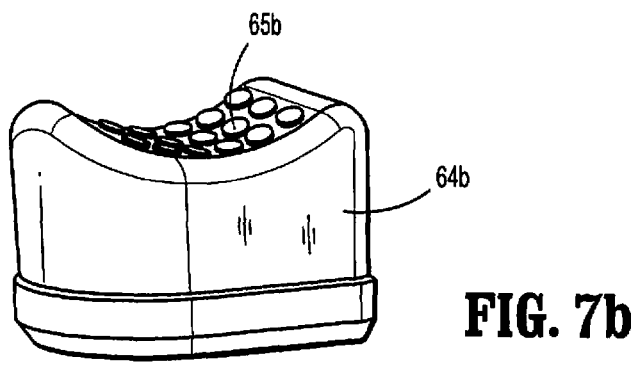
FIG. 7b is a view of another embodiment of a finger pad of an improved finger exerciser in accordance with the present disclosure.
Figure 7C:
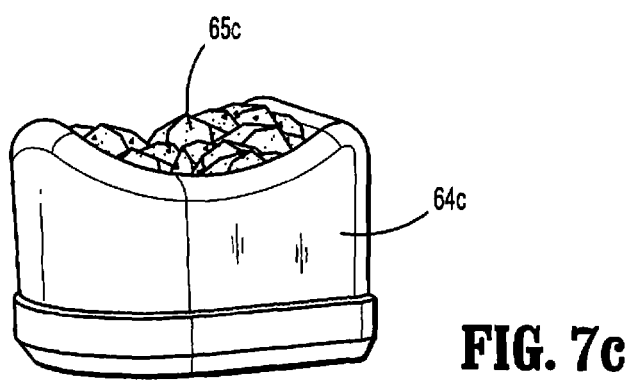
FIG. 7c is a view of yet another embodiment of a finger pad of an improved finger exerciser in accordance with the present disclosure.
Figure 7D:
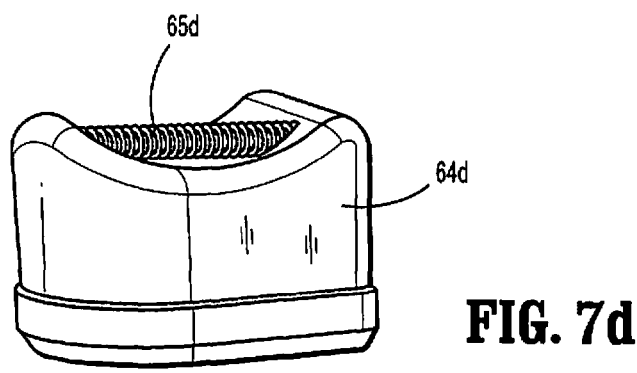
FIG. 7d is a view of still another embodiment of a finger pad of an improved finger exerciser in accordance with the present disclosure.

Turning now to FIGS. 7a, 7b, 7c, and 7d, example embodiments of alternative finger pads are shown which include a specialized textured finger-contacting surface for enhancing particular training regimens, such as without limitation, exercises addressing neurological disorders, rock-climbing training, callous-building exercises (for, e.g., guitarists), etc. FIG. 7a shows a finger pad 64a that includes a finger contacting surface having a crosshatch pattern 65a. FIG. 7b shows a finger pad 64b that includes a finger contacting surface having a coarse, nubbed texture 65b. FIG. 7c shows a finger pad 64c that includes a finger contacting surface having a rock-like surface 65c. In embodiments, rock, sand, gravel and/or other mineral compositions may be embedded in finger pad 64c to form surface 65c. FIG. 7d shows a finger pad 64d that includes a finger contacting surface that includes a musical instrument string 65d and/or a musical instrument string-like structure protruding therefrom. As described above, such alternative finger pads may be selectively coupled to pad base 35 for use.

Figure 8:
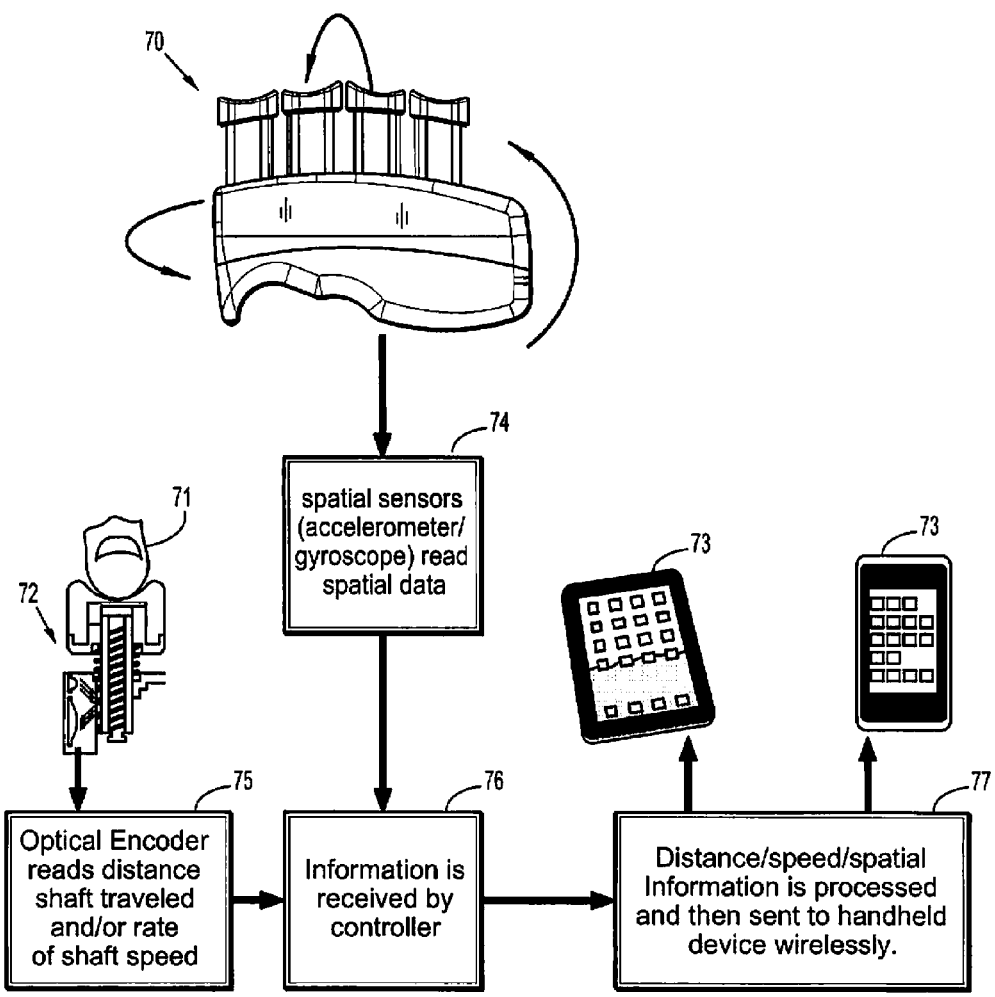
FIG. 8 is a schematic diagram of an embodiment of a finger exercise system in accordance with the present disclosure.

With reference to FIG. 8, in another aspect a finger exercise system is disclosed in which finger exerciser 70 is in communication with a handheld device 73. During use, data relating to an exercise being performed is received by a controller. In the example embodiment shown in FIG. 8, positional motion of a finger exerciser 70 is sensed by spatial sensor 74 (accelerometer, gyroscope, compass, etc.) and communicated to a controller 76. Additionally or alternatively, an optical positional encoder 75 senses the movement of plunger assembly 72 by a user's finger 71, and communicated the positional data to controller 76. Controller 76 communicates spatial and positional data wirelessly through a wireless interface 77, which may include a Bluetooth® transceiver, to a handheld device 73. Handheld device 73 includes an application program ("app") that is programmed to collect and display the spatial and positional exercise data. In embodiments, the handheld device includes the capability of recording the collected data, tracking performance of a use, and communicating exercise data to an evaluating entity, such as a hand therapist, guitar teacher, etc., for analysis.

Figure 9:
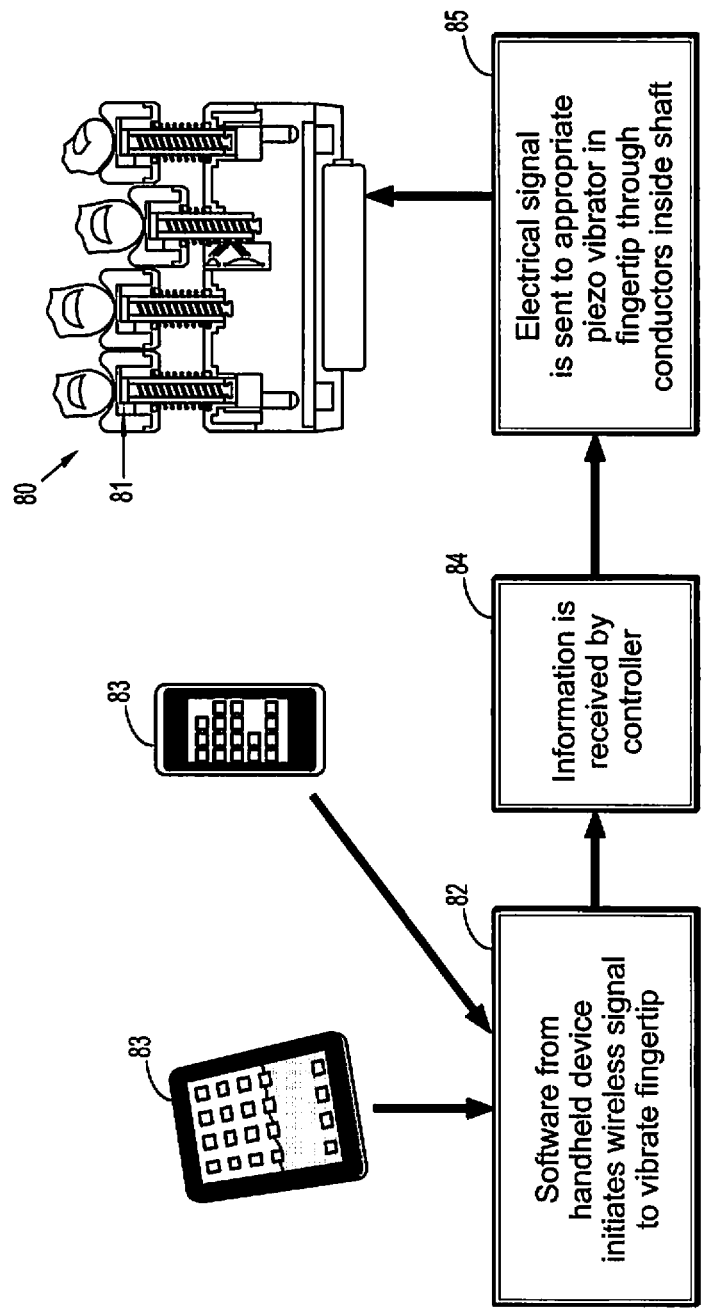
FIG. 9 is a schematic diagram of another embodiment of a finger exercise system in accordance with the present disclosure.

With reference to FIG. 9, in another aspect a finger exercise system is disclosed in which finger exerciser 80 is in communication with a handheld device 83. During use, application 82 executing on handheld device 83 communicates commands to a communications interface 84 of a controller 85 included within finger exerciser 80 to cause a finger pad transducer 81 to vibrate, sending tactile stimulation to the user's fingertip(s). In embodiments, application 82 includes the capability of receiving user input to select, define, and/or store an exercise routine. Application 82 may directly control the sequence of finger stimulation events in real time, or may download a routine to finder exerciser 80 for execution by controller 85.

Figure 10C:
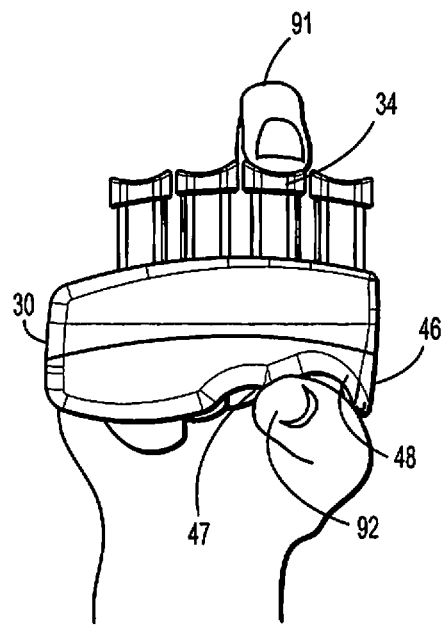
FIG. 10c is still another view of an embodiment of an improved finger exerciser in use in accordance with the present disclosure.
Figure 10D:
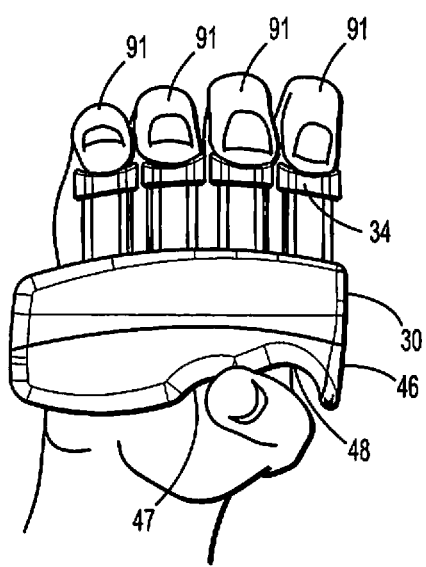
FIG. 10d is a yet another view of an embodiment of an improved finger exerciser in use in accordance with the present disclosure.
Figure 10E:
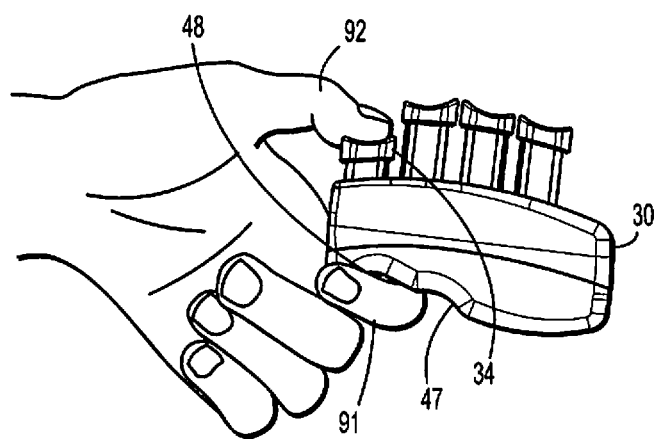
FIG. 10e is a view of an embodiment of an improved finger exerciser in use to exercise a thumb in accordance with the present disclosure.

Turning now to FIGS. 10a-10e, various methods of use of a finger exerciser 30 in accordance with the present disclosure are illustrated. In FIG. 10a, a user places finger exerciser 30 in the hand, such that grip 46 rests generally in the palm and base 92' of thumb 92 rests within thumb saddle 47. In FIG. 10b the user's hand is closed around finger exerciser 30 and fingertips 91 are placed on finger pads 34. In the FIG. 10b configuration the primary focus of the finger exercise are the user's four fingers 91. In the configuration shown in FIGS. 10c and 10d, the tip of the user's thumb 92 is placed into thumb saddle 47 and/or finger saddle 48. As shown in FIG. 10c, an exercise routine targeted to the user's middle finger and thumb is illustrated. Advantageously, the contours of thumb saddle 47 and finger saddle 48 enable a user to grasp finger exerciser 30 in a manner which enables the targeted exercise to be performed ergonomically and which may provide improved physiological benefits. FIG. 10d shows another configuration wherein the finger exercise is targeted to the index, middle, ring, pinky finger, and thumb, with the thumb squarely placed in thumb saddle 47. In FIG. 10e, yet another configuration is shown wherein a user's index finger 91 is placed within finger saddle 48 and the tip of the user's thumb 92 is placed in a finger pad 34 to perform an exercise routine targeted to the user's thumb 92.

The described embodiments of the present disclosure are intended to be illustrative rather than restrictive, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. An improved finger exerciser, comprising:
    a housing having an upper portion and a lower portion;
    a plunger assembly comprising:
        a tubular shaft having an outer surface that is entirely continuous, the tubular shaft supporting a pad base on an upper end thereof; and
        a finger pad operably engaged with the pad base;
    an opening defined in the upper portion of the housing configured to enable the tubular shaft to traverse therethrough;
    a coil spring in operative association with the tubular shaft and configured to urge the tubular shaft in an upward direction; and
    a grip defined in the lower portion of the housing, the grip comprising:
        a first concave portion forming a thumb saddle defined in the grip;
        a second concave portion forming a finger saddle defined in the grip; and
        a convex portion forming a palm pad defined on the grip.

2. The improved finger exerciser in accordance with claim 1, further comprising a shaft guide configured to slidably extend into an inner bore of the tubular shaft.

3. The improved finger exerciser in accordance with claim 2, wherein the shaft guide extends from a guide frame.

4. The improved finger exerciser in accordance with claim 2, wherein the coil spring is concentrically disposed between the inner bore of the tubular shaft and an outer surface of the shaft guide.

5. The improved finger exerciser in accordance with claim 1, further comprising a controller configured to communicate with a motion detection and encoding assembly.

6. The improved finger exerciser in accordance with claim 5, wherein the controller further comprises a data communication interface.

7. The improved finger exerciser in accordance with claim 5, wherein the motion detection and encoding assembly includes a linear position encoder in operative association with the tubular shaft and in operable communication with the controller.

8. The improved finger exerciser in accordance with claim 7, wherein the linear position encoder comprises:
    a scale fixed on the outer surface of the tubular shaft having encoded indicia disposed thereupon;
    a light source configured to illuminate the scale; and
    a light detector configured to detect reflected light from the scale.

9. The improved finger exerciser in accordance with claim 5, wherein the motion detection and encoding assembly includes a piezoelectric transducer fixed to the pad base and in operable communication with the controller.

10. The improved finger exerciser in accordance with claim 9, wherein the controller includes:
    a processor; and
    a memory in operable communication with the processor and comprising a set of programmed instructions executable on the processor to vibrate the piezoelectric transducer in accordance with a predetermined pattern.

11. A finger exercising system, comprising:
    a finger exerciser, comprising:
        a housing having an upper portion and a lower portion;
        a plunger assembly comprising:
            a tubular shaft having a pad base defined at an upper end thereof; and
            a finger pad operably engaged with the pad base;
        an opening defined in the upper portion of the housing configured to enable the tubular shaft to traverse therethrough;
        a coil spring in operative association with the tubular shaft and configured to urge the tubular shaft in an upward direction; and
        a grip defined in the lower portion, the grip comprising:
            a first concave portion forming a thumb saddle defined in the grip;
            a second concave portion forming a finger saddle defined in the grip; and
            a convex portion forming a palm pad defined on the grip;
        a controller configured to communicate with at least one of a linear position encoder, a spatial sensor, and a transducer and having a data communication interface configured to communicate with a remote handheld device;
    a software application executable on a remote handheld device and configured to communicate with the controller to perform an action selected from the group consisting of receiving a linear position, receiving a spatial parameter, storing a linear position, storing a spatial parameter, displaying a linear position, displaying a spatial parameter, and transmitting a transducer command.

12. The finger exercising system in accordance with claim 11, wherein the spatial sensor is selected from the group consisting of a silicon accelerometer, a silicon gyroscope, and a silicon compass.

13. The finger exercising system in accordance with claim 11, wherein the software application is configured to communicate a linear position and/or a spatial parameter to an evaluating entity.

14. The finger exercising system in accordance with claim 11, wherein the linear position encoder is configured to encode a position of the tubular shaft.

15. The finger exercising system in accordance with claim 11, further comprising a piezoelectric transducer fixed to the pad base and in operable communication with the controller and/or the software application.

16. A method of operating a hand exerciser, comprising:
    providing a hand exerciser, comprising a finger-actuatable plunger having a finger-contacting portion and a biasing member that urges the finger-actuatable plunger against finger pressure;
    performing a gesture comprising depressing the finger-actuatable plunger to initiate an exercise routine; and
    causing the finger-contacting portion of the plunger to vibrate.

17. The method of operating a hand exerciser in accordance with claim 16, wherein causing the finger-contacting portion of the plunger to vibrate comprises vibrating the finger-contacting portion of the plunger in a predetermined pattern corresponding to the exercise routine.

18. The method of operating a hand exerciser in accordance with claim 16, further comprising selecting the exercise routine from a set of predetermined exercise routines in response to a performed gesture.

19. The method of operating a hand exerciser in accordance with claim 16, further comprising measuring a displacement of the tubular shaft and/or a velocity of the tubular shaft.

20. The method of operating a hand exerciser in accordance with claim 19, further comprising wirelessly communicating measured displacement and/or velocity to a remote device.

21. The improved finger exerciser in accordance with claim 1, the tubular shaft further defining a continuous inner bore.

22. The improved finger exerciser in accordance with claim 2, wherein the tubular shaft completely surrounds the shaft guide while the shaft guide is extended into the inner bore of the tubular shaft.

23. The improved finger exerciser in accordance with claim 2, wherein the shaft guide is substantially tubular.

24. The finger exercising system in accordance with claim 11, the tubular shaft further comprising a continuous outer surface.

25. The finger exercising system in accordance with claim 11, the tubular shaft further defining a continuous inner bore.

26. The finger exercising system in accordance with claim 11, the plunger assembly further comprising a shaft guide configured to slidably extend into an inner bore of the tubular shaft.

27. The finger exercising system in accordance with claim 26, wherein the tubular shaft completely surrounds the shaft guide while the shaft guide is extended into the inner bore of the tubular shaft.

28. The finger exercising system in accordance with claim 26, wherein the shaft guide is substantially tubular.

29. An improved finger exerciser, comprising:
a housing having an upper portion and a lower portion, the upper portion defining an opening, the lower portion defining a grip;
a plunger assembly comprising:
a tubular shaft having an outer surface that is entirely continuous, the tubular shaft having a pad base defined at an upper end thereof, the tubular shaft configured to traverse through the opening of the housing; and
a finger pad operably engaged with the pad base; and
a coil spring in operative association with the tubular shaft and configured to urge the tubular shaft in an upward direction.

30. A finger exercising system, comprising:
a finger exerciser, comprising:
a housing having an upper portion and a lower portion, the upper portion defining an opening, the lower portion defining a grip;
a plunger assembly comprising:
a tubular shaft having a pad base defined at an upper end thereof, the tubular shaft configured to traverse through the opening of the housing; and
a finger pad operably engaged with the pad base; and
a coil spring in operative association with the tubular shaft and configured to urge the tubular shaft in an upward direction; and
a controller configured to electrically communicate with the finger exerciser.

31. The finger exercising system of claim 30, wherein the controller is configured to communicate with a motion detection and encoding assembly including a sensor, an encoder, a circuit, a potentiometer, a diode, a detector, or combinations thereof.

* * * * *